United States Patent [19]

Kurtz et al.

[11] 4,396,386
[45] Aug. 2, 1983

[54] SURGICAL DRAINAGE APPARATUS WITH SUCTION CONTROL AND INDICATION

[75] Inventors: Leonard D. Kurtz, Woodmere; Joseph M. LiCausi, Port Jefferson Sta., both of N.Y.

[73] Assignee: BioResearch Inc., Farmingdale, N.Y.

[21] Appl. No.: 261,476

[22] Filed: May 7, 1981

[51] Int. Cl.³ .............................................. A61M 1/00
[52] U.S. Cl. .................................... 604/318; 604/319
[58] Field of Search .............. 128/276, 277, 278, 281, 128/760; 116/268, 272; 73/714, 715; 604/118, 119, 319-321, 318; 137/205

[56] References Cited

U.S. PATENT DOCUMENTS

| | | | |
|---|---|---|---|
| 2,135,148 | 11/1938 | Roy | 128/277 |
| 3,363,626 | 1/1968 | Bidwell et al. | 128/276 |
| 3,750,692 | 8/1973 | Tibbs | 128/276 |
| 4,020,525 | 5/1977 | Fromknecht et al. | 116/268 |
| 4,193,292 | 3/1980 | Simonsson | 116/268 |

FOREIGN PATENT DOCUMENTS

| | | | |
|---|---|---|---|
| 1069409 | 1/1980 | Canada | 128/276 |
| 66491 | 4/1969 | German Democratic Rep. | 128/276 |

OTHER PUBLICATIONS

"Bellows" Websters New Collegiate Dictionary, Springfield, Mass., 1961, p. 80.

Primary Examiner—Richard J. Apley
Assistant Examiner—J. L. Kruter
Attorney, Agent, or Firm—Larson and Taylor

[57] ABSTRACT

A surgical drainage unit is provided for draining fluids from the body of a patient wherein the suction pressure, applied through a suction inlet of the unit to draw fluids into the unit, is controlled and a direct indication of the applied suction pressure is afforded. A device which contracts responsive to an increase in suction in a collection chamber of the unit is equipped with an indicator vane that cooperates with a fixed scale to indicate the amount of movement of the bellows and hence indicate the suction within the collection chamber. A manually adjustable control valve controls the amount of air admitted to the suction line within the unit to thereby control the applied suction.

10 Claims, 3 Drawing Figures

SURGICAL DRAINAGE APPARATUS WITH SUCTION CONTROL AND INDICATION

FIELD OF THE INVENTION

The present invention relates to surgical drainage devices used in draining fluids from the body, e.g. the pleural cavity, and is particularly concerned with an improved drainage apparatus which provides ready control of the applied suction pressure.

BACKGROUND OF THE INVENTION

It is essential for normal breathing that the space within the pleural cavity surrounding the lungs be free of liquid and be subject to a negative pressure so as to draw the lungs outwardly to fill this pleural cavity in order to permit proper breathing. Any invasion of the pleural cavity such as caused by lung surgery or foreign objects which pierce the ribcage, or such as occur, for example, where the patient has pleurisy, generates fluids in the pleural cavity which tend to obstruct normal breathing. It is necessary to provide a device which can remove these fluids from the pleural cavity and at the same time ensure that the desired degree of negative pressure is maintained within the pleural cavity.

One of the basic types of apparatus which has been used for this purpose is shown, for example, in U.S. Pat. Nos. 3,363,626 and 3,363,627. This apparatus is known as an underwater drainage apparatus and provides three chambers, one chamber comprising a collection chamber for collecting the fluids drained from the pleural cavity through a thoracotomy tube, a second chamber known as an underwater seal chamber which protects the pleural cavity from being subject to atmospheric pressure, and a third chamber known as a pressure manometer chamber which serves to regulate the degree of negative pressure within the pleural cavity. This type of apparatus has been highly successful in both removing fluids from the pleural cavity and in maintaining the desired degree of negativity within the pleural cavity.

However, an apparatus such as disclosed in the patents referred to requires prefilling of the underwater seal chamber with water as well as prefilling the pressure manometer chamber to the desired level to maintain the desired degree of negativity within the pleural cavity. It is obvious that it would be desirable to eliminate the need for filling the underwater seal and manometer chambers particularly in emergency situations but also in general use, in that the less a user of the apparatus has to do with the operation the less likely it is that something will be done improperly, i.e. the greater the active participation the greater the chance for human error.

Although drainage devices have been developed which do not require a filling of the underwater seal chamber (see, for example, U.S. Pat. No. 4,015,603), these devices generally do not provide a direct indication of the suction force being exerted. Such a feature is, of course, highly desirable in a drainage device.

SUMMARY OF THE INVENTION

In accordance with the invention an improved medical drainage device for draining fluids from the body of a patient is provided which enables the operator to control the suction being applied and which affords a direct indication of the suction pressure being applied to the suction chamber so the applied suction can be closely controlled. The suction pressure control and indicator arrangement is simple and rugged in construction and efficient and dependable in use. According to the invention, the surgical drainage apparatus comprises a container which is connected to a suction source so that fluids can be drawn into the container, a fluid inlet in the container, a collection chamber for collecting the fluids drawn into the container through the fluid inlet, a manually controllable variable control device for controlling the amount of suction created within the container, and an indicator arrangement responsive to the suction pressure created within the collection chamber for providing an indication of the applied suction. The apparatus of the invention is completely "dry" prior to use, i.e., does not require any prefilling by a user.

In a preferred embodiment of the invention, the basic component of the indicator arrangement is a bellows which is connected to the collection chamber of the drainage device and which contracts with increased suction in the collection chamber. A scale cooperates with a pointer or indicator attached to the bellows to provide an indication of the suction. In this preferred embodiment, the controllable, variable control device comprises a control valve which is disposed in an air line connected to the suction line within the container and which controls the amount of air supplied to the suction line and hence the suction pressure. An air flow control knob associated with the control valve enables the operator to "dial in" the desired pressure, and thus with the direct reading of the applied suction pressure provided by the indicator arrangement to the operator during adjustment of the control knob the suction can be closely controlled. A restrictor located in the suction line within the unit further controls the suction pressure, enabling the unit to be directly connected to wall suction.

Other features and advantages of the invention will be set forth in, or apparent from, the detailed description of a preferred embodiment found hereinbelow.

DESCRIPTION OF THE PREFERRED EMBODIMENTS

Figure 1:
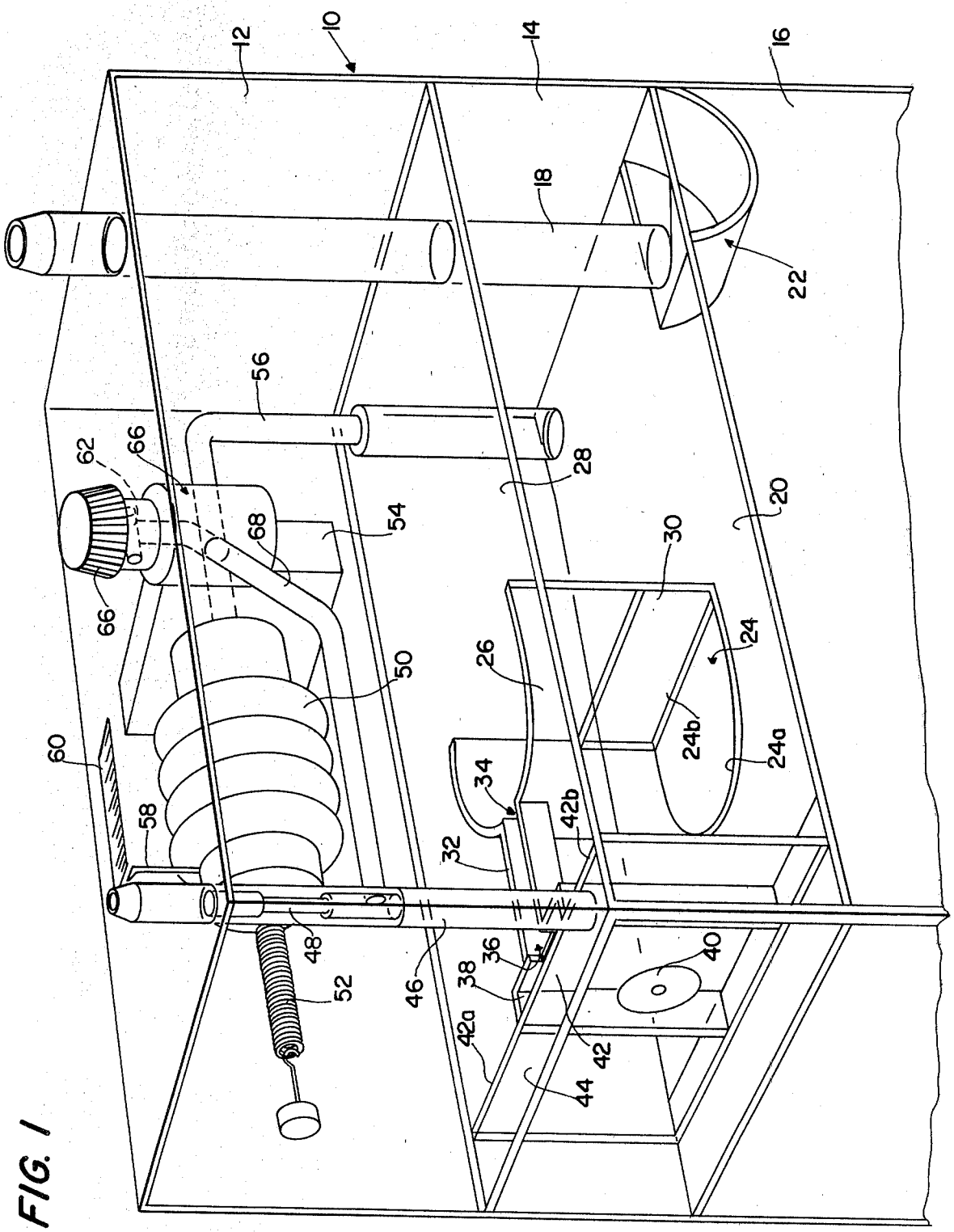
FIG. 1 is a perspective view of a drainage device constructed in accordance with the invention.
Figure 2:
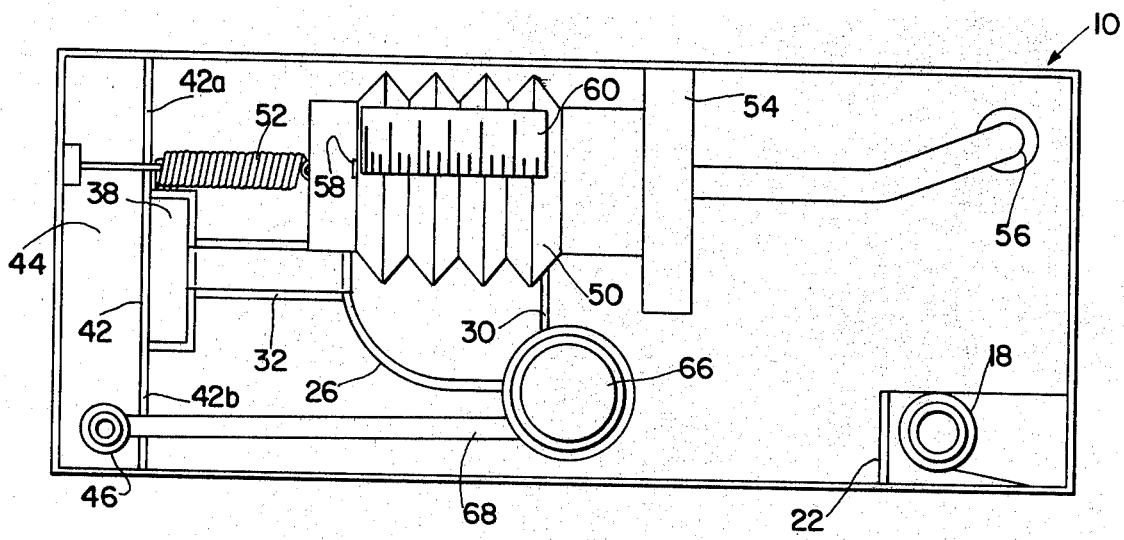
FIG. 2 is a plan view of the drainage device of FIG. 1.
Figure 3:
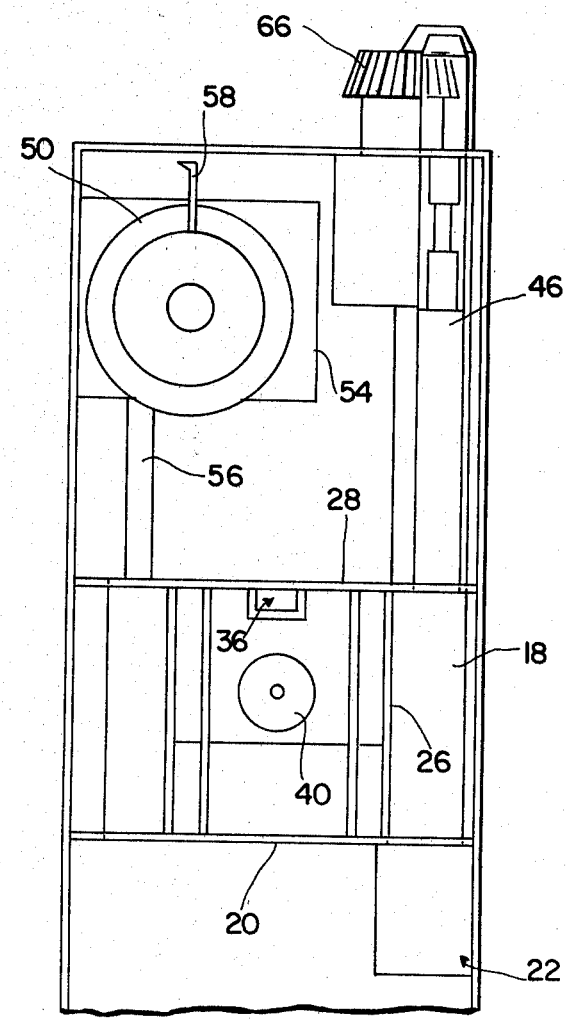
FIG. 3 is an end view of the drainage device of FIG. 1.

Referring to the drawings, a preferred embodiment of the invention is shown. The drainage device of this embodiment basically comprises a housing 10 having three separate chambers, formed therein. These chambers comprise an upper, suction control chamber 12, an intermediate, combined fluid seal-collection chamber 14 and a lower, main, collection chamber 16. The latter, i.e., chamber 16, merely comprises a container formed at the bottom of housing 10 for the collection of fluids drawn or sucked in by the drainage device and need not be additionally described. Further, the combined fluid seal-collection chamber 14 is of the type described in commonly assigned U.S. patent application Ser. No. 107,329 which was filed on Dec. 26, 1979, now U.S. Pat. No. 4,312,351, issued Jan. 26, 1982 and the subject matter of which is hereby incorporated by reference, and reference is made to that application for a more complete description of this feature. However, for the sake of completeness, chamber 14 will also be briefly described here, together with upper chamber 12.

Chamber 14 includes therein a portion of an inlet tube 18 which also extends through chamber 12 and which is adapted to be connected to the patient through a thoracotomy tube (not shown). The lower floor partition 20 of chamber 14 (which divides housing 10 into chambers 14 and 16) includes a recessed "cup" portion 22 into which inlet 18 opens. An aperture or opening 24 in floor partition 20 permits flow of fluids out of chamber 14 into chamber 16. Opening 24 is bounded along a generally semi-circular edge 24a by a wall 26 which is in the form of a half-cylinder and extends between lower chamber floor partition 20 and a ceiling partition 28 (which divides housing 10 into chambers 12 and 14). A "gate" member 30 extends upwardly from a straight line edge of opening 24 a distance roughly one-third the height of wall 26. A passage way 32 is provided between an opening 34 in wall 26 and a corresponding opening 36 in a further wall of a suction valve chamber 38.

The vertical walls of chamber 38 extend between horizontal partitions 20 and 28 and chamber 38 communicates with a one-way valve device 40 located in a wall 42 between chamber 38 and a suction valve outlet chamber 44, wall 42 being common to chambers 38 and 44. The wall 42, and laterally extending wall portions denoted 42a, 42b, separate valve chamber 44 from the remainder of chamber 14. Valve chamber 44 is connected to a suction tube 46 which extends through upper chamber 12 and which is adapted to be connected to wall suction. Thus, air can be drawn out of chamber 12 (and chamber 16) through the path which includes opening 34, passageway 32, opening 36, chamber 38, valve 40, outlet chamber 44 and suction tube 46.

Suction control chamber 12 includes a bellows 50 mounted therein which is connected through a spring 52 to one end wall of housing 10. The other fixed end of bellows 50 is supported in chamber 12 by a flange 54 extending from a side wall of housing 10. An L-shaped inlet tube 56 connects bellows 50 with collection chamber 16, the upright leg of tube 56 extending from suction control chamber 12 through intermediate chamber 14 to chamber 16. The movable end of bellows 50 includes an indicator vane 58 mounted thereon which cooperates with a scale 60 provided on the upper wall of housing 10 to indicate the imposed suction. In practice, in the exemplary embodiment under consideration, the imposed suction will vary from about $-10$ cm $H_2O$ to about $-100$ cm $H_2O$. Chamber 12 is at atmospheric pressure and thus bellows 50 contracts when suction is applied thereto through inlet tube 56. The amount of contraction is proportional to the applied suction and thus indicator vane 58 in cooperation with scale 60 provides a direct reading of the suction applied to the unit.

An atmospheric inlet control valve 62 includes an opening 64 which is open to ambient atmosphere and a control knob 66 which controls the amount of air flow to an outlet tube 68. Control valve 62 can be of any suitable conventional construction wherein rotation of the control knob 66 controls the air flow through the valve. Air tube 68 is connected to suction tube 46 and thus control knob 66 can be used to "dial in" the desired suction, the variation in the air flow to suction tube 56 determining the amount of suction applied to the unit. It will be appreciated that the greater the inlet air flow as dictated by control valve 62, the lower the resultant suction.

It is noted that the wall suction in a hospital or like facility is always at a "wide open" setting and typically varies between 200 mm Hg and 750 mm Hg deadhead. This amount of suction can obviously cause problems, and to overcome these problems and permit the device of the invention to be directly connected to wall suction without controlling or modifying the latter, a restrictor 48 is provided in suction line 46. The restrictor 48 is sized such that with the control valve 62 wide open (maximum air), the imposed suction will be about $-10$ cm $H_2O$. Many practitioners prefer a suction level of about $-20$ cm $H_2O$ while others desire a higher level, e.g., $-100$ cm $H_2O$. The restrictor 48 in combination with control valve 62 provides the range discussed above, i.e., from about $-10$ cm $H_2O$ to about $-100$ cm $H_2O$. It has been found that for a quarter-inch (0.250" diameter) outflow suction control line, satisfactory results have been obtained where the size of the restriction ranges between about 0.050" and 0.187". In general, the restriction provided by restrictor 48 should not be so great that, with valve 62 wide open, the desired minimum negativity cannot be achieved.

In summary, suction control chamber 12 provides an indication of the suction applied to the unit and enables control of the applied suction. In this regard, the use of control valve 66 in cooperation with the indicator formed by scale 60 and vane 58 enables one to readily adjust the suction using control knob 66.

Although the invention has been described relative to an exemplary embodiment thereof, it will be understood that variations and modifications can be effected in this embodiment without departing from the scope and spirit of the invention.

We claim:

1. A surgical pleural underwater drainage apparatus which is dry prior to use for draining fluids from the body of a patient, said apparatus comprising:
    a container,
    a fluid inlet in said container;
    a collection chamber formed in said container for collecting fluids received through said fluid inlet;
    connection means for connecting said container to a suction source so as to create a suction within said container and thereby draw fluids into said container through said fluid inlet;
    manually controllable means for providing a passageway of variable size for admitting air to said connection means for controlling the amount of suction created within the collection chamber of said container; and
    expansible proportional indicator means, located in an upper chamber within said container and responsive to the suction created within said collection chamber, for providing an indication of the level of suction created.

2. Apparatus as claimed in claim 1 wherein said indicating means comprises pressure responsive devices located within the upper chamber at ambient atmosphere pressure within said container, said device being connected to said collection chamber and including an indicator member whose movement is proportional to the suction created in the collection chamber.

3. Apparatus as claimed in claim 2 wherein said pressure responsive device comprises a bellows which contracts responsive to an increase in suction and said indicator member comprises an indicator vane attached to said bellows, said indicating means further comprising a scale which cooperates with said indicator vane to provide an indication of the suction created.

4. Apparatus as claimed in claim 3 further comprising spring means for mounting one end of said bellows to permit expansion and contraction of said bellows, said spring means including a spring connected between the said one end of said bellows and a wall of said container.

5. Apparatus as claimed in claim 1 or claim 2 wherein said connection means comprises means defining a passageway for suction air between the collection chamber and a suction inlet, said manually controllable means comprises a control valve which controls the admission of ambient atmospheric air to said passageway so as to control the suction created within said collection chamber.

6. Apparatus as claimed in claim 5 wherein said control valve includes a manually variable control knob for controlling atmospheric air flow.

7. Apparatus as claimed in claim 6 wherein said passageway includes a suction tube and said control valve is connected by a further tube to said suction tube.

8. Apparatus as claimed in claim 1 or claim 2 wherein said connection means includes a suction tube having a restrictor means mounted therein for restricting the suction air flow in said suction tube.

9. Apparatus as claimed in claim 8 wherein said variable control means comprises a control valve for controlling the admission of ambient atmospheric air to said apparatus and wherein the suction air flow restriction provided by said restrictor means is such to enable a minimum negativity of $-10$ cm $H_2O$ to be achieved with said control valve in a position wherein maximum ambient atmospheric air is admitted to said apparatus.

10. Apparatus as claimed in claim 9, wherein said restriction means in combination with said control valve controls the suction to a value within an operating range of $-10$ cm $H_2O$ to $-100$ cm $H_2O$.

* * * * *